(12) United States Patent
Woudenberg et al.

(10) Patent No.: US 6,660,147 B1
(45) Date of Patent: *Dec. 9, 2003

(54) HIGH DENSITY ELECTROPHORESIS DEVICE AND METHOD

(75) Inventors: Timothy M. Woudenberg, Moss Beach, CA (US); Reid B. Kowallis, Burlingame, CA (US)

(73) Assignee: Applera Corporation, Foster City, CA (US)

(*) Notice: Subject to any disclaimer, the term of this patent is extended or adjusted under 35 U.S.C. 154(b) by 613 days.

This patent is subject to a terminal disclaimer.

(21) Appl. No.: 09/616,596

(22) Filed: Jul. 14, 2000

Related U.S. Application Data
(60) Provisional application No. 60/144,103, filed on Jul. 16, 1999.

(51) Int. Cl.$^7$ .................. G01N 27/26; G01N 27/447
(52) U.S. Cl. .................. 204/455; 204/450; 204/451; 204/600; 204/601; 204/605; 435/288.5; 435/288.6
(58) Field of Search .................. 204/451, 452, 204/453, 454, 455, 601, 602, 603, 604, 605, 450, 600; 435/288.5, 288.6

(56) References Cited

U.S. PATENT DOCUMENTS

| | | | |
|---|---|---|---|
| 4,374,723 A | | 2/1983 | Vesterberg |
| 4,670,119 A | | 6/1987 | Hurd |
| 5,483,075 A | | 1/1996 | Smith et al. |
| 5,858,804 A | * | 1/1999 | Zanzucchi et al. ........... 436/536 |
| 5,872,010 A | | 2/1999 | Karger et al. |
| 6,013,513 A | * | 1/2000 | Reber et al. ............. 435/288.5 |
| 6,100,535 A | | 8/2000 | Mathies et al. |
| 6,126,804 A | * | 10/2000 | Andresen .................... 204/601 |
| 6,132,579 A | * | 10/2000 | Edwards et al. ............ 204/451 |
| 6,143,152 A | * | 11/2000 | Simpson et al. ............ 204/451 |
| 6,207,031 B1 | * | 3/2001 | Adourian et al. ........... 204/451 |
| 6,319,469 B1 | * | 11/2001 | Mian et al. .................... 422/64 |

FOREIGN PATENT DOCUMENTS

| | | |
|---|---|---|
| EP | 0 153 017 B1 | 6/1987 |
| EP | 0 376 611 A2 | 7/1990 |

(List continued on next page.)

OTHER PUBLICATIONS

Simpson et al., "High–Performance Microfabricated Capillary Array Electrophoresis Systems for DNA Analysis," *SPIE*, vol. 3258, pp. 170–180, (1998).

(List continued on next page.)

*Primary Examiner*—Nam Nguyen
*Assistant Examiner*—John S. Starsiak, Jr.
(74) *Attorney, Agent, or Firm*—Vincent M. Powers

(57) ABSTRACT

The present invention provides, in one aspect, an apparatus for electrophoretic separation of analytes. In one aspect, the apparatus comprises a disc-shaped substrate defining (1) a central reservoir region, (2) a plurality of electrophoretic channels in fluid communication with, and emanating substantially radially from, the central reservoir region, the channels being coplanar with each other, and each channel having (i) a proximal end which is linked to the reservoir region, and (ii) a distal end, and preferably (3) for each channel, at least one chamber, and preferably three chambers, linked by a passageway in fluid communication with the distal end of that channel. Preferably, each passageway leads from each chamber in a direction that is initially away from the central reservoir region, whereby centrifugation of the substrate about a central axis that is perpendicular to the channels is effective to disperse liquid from the central reservoir region into the channels and chambers, such that any air bubbles in the chambers, channels, and passageways are forced towards the axis of rotation, when such liquid is present in the central reservoir region.

23 Claims, 7 Drawing Sheets

FOREIGN PATENT DOCUMENTS

| | | |
|---|---|---|
| EP | 0 376 611 A3 | 7/1990 |
| WO | WO 83/01906 A1 | 6/1983 |
| WO | WO 95/06508 A1 | 3/1995 |
| WO | WO 95/06870 A1 | 3/1995 |
| WO | WO 96/04547 A1 | 2/1996 |
| WO | WO 99/24827 A1 | 5/1999 |
| WO | WO 99/39193 A1 | 8/1999 |

OTHER PUBLICATIONS

Freemantle, "Downsizing Chemistry—Chemical Analysis and Synthesis on Microchips Promise a Variety of Potential Benefits," *Chemical & Engineering News*, pp. 27–36, Feb. 22, 1999.

International Search Report from PCT/US00/19265.

* cited by examiner

HIGH DENSITY ELECTROPHORESIS DEVICE AND METHOD

This application claims the benefit of priority under 35 U.S.C. 119(e) to prior application Ser. No. 60/144,103 filed Jul. 16, 1999, which is incorporated herein by reference.

FIELD OF THE INVENTION

The present invention relates to electrophoretic analysis of analytes of interest. More particularly, the invention relates to small-scale devices for conducting electrophoretic separation and/or analysis of analytes, as well as chemical and biochemical methods employing such devices.

REFERENCES

Bergot et al., PCT Pub. No. WO 91/07507.

Eckstein, F., *Oligonucleotides and Analogs: A Practical Approach*, Chapters 8 and 9, IRL Press, Oxford, GB (1991).

Fodor, S. P .A., et al., U.S. Pat. No. 5,445,934 (1995).

Fung et al, U.S. Pat. No. 4,757,141.

Grossman, P. D., and J. C. Colburn (eds.), *Capillary Electrophoresis: Theory and Practice*, Academic Press, Inc., London, UK (1992).

Haugland, *Handbook of Fluorescent Probes and Research Chemicals*, Molecular Probes, Inc., Eugene, Oreg. (1992).

Hobbs, Jr., et al., U.S. Pat. No. 5,151,507.

Huang, X. C., et al., *Anal. Chem.* 64:967 (1992).

Jackson, P., PCT Pub. No. WO 91/05256.

Keller and Manak, *DNA Probes, 2nd Ed.*, Stockton Press, New York (1993).

Kheterpal et al., *Eletrophoresis* 17:1852–1859 (1996).

Landegren et al., U.S. Pat. No. 4,988,617.

Lee et al., EP 805190 A2 (1997).

Livak et al., PCT App. No. PCT/US98/09657.

Madou, M., *Fundamentals of Microfabrication*, CRC Press, LLC, Boca Raton, Fla. (1997).

Mathies, R. A., et al., U.S. Pat. No. 5,091,652 (1992).

Matthews et al, *Anal. Biochem.* 169:1–25 (1988).

Menchen, S., et al., PCT Pub. No. WO 94/05688 (1994).

Menchen, S., et al., U.S. Pat. No. 5,188,934 (1993).

Pastinen, T., et al., *Genome Res.* 7:606–614 (1997).

Rosenblum et al., *Nucl. Acids Res.* 25:4500–4504 (1997).

Sze, S. M., ed., *VLSI Technology, $2^{nd}$ Ed.*, McGraw-Hill Publishing, New York, N.Y. (1988).

Whiteley et al., U.S. Pat. No. 4,883,750.

BACKGROUND

The structural analysis of polynucleotides and other biomolecules is playing an increasingly important role in modern molecular biology. With the advent of polynucleotide amplification technology, e.g., PCR, and projects directed towards sequencing the human genome, the level of interest in this area is high. In particular, the need to process large numbers of samples as quickly as possible has led to the need for analytical systems with increased resolution, throughout, and automation.

It would be desirable to have a device which permits efficient, large-scale analysis of many samples in as small an area as possible, in order to reduce cost and the amount of sample manipulation. At the same time, the device should provide reproducible, high sensitivity detection of analytes of interest. Preferably, the device will be compatible with a variety of different sample types and will be amenable to re-use with different sample sets.

SUMMARY

In one aspect, the present invention provides an apparatus for electrophoretic separation of analytes. In a preferred embodiment, the apparatus comprises a planar substrate defining (1) a central reservoir region, (2) a plurality of electrophoretic channels in fluid communication with, and emanating substantially radially from, the central reservoir region, the channels being coplanar with each other, and each channel having (i) a proximal end which is linked to the reservoir region, and (ii) a distal end. At the distal end of each channel, the substrate further defines at least one chamber linked in fluid communication with the distal end of the channel. For example, each channel can be linked to a sample chamber, a sample-receiving chamber, and a running buffer chamber. Alternatively, each channel can be linked to two distal chambers. Each one or more chambers is preferably linked to the distal end of a channel by a passageway that leads from each chamber in a direction that is initially away from the central reservoir region, whereby centrifugation of the substrate about a central axis that is perpendicular to the channels is effective to disperse liquid from the central reservoir region into the channels and chambers, such that any air bubbles in the chambers, channels, and passageways are forced towards the axis of rotation, when such liquid is present in the central reservoir region.

The apparatus preferably includes electrodes for applying a voltage potential between the chambers and the central reservoir. The apparatus may also include a detector for detecting selected components which may be present in the channels. In one embodiment, the detector and substrate are disposed such that the detector and/or substrate are rotatable relative to each other to permit rotary detection. For example, in one approach, the detector can be rotatable about a central axis within the central reservoir region, for detecting signal emission from each of the channels at a selected distance from the axis, or along a selected length of each channel. In an alternate embodiment, the substrate may be rotatable about a central axis such that the channels pass sequentially by the detector, for detecting one or more components that may be present in the channels. In a preferred embodiment, the detector is adapted for detecting a fluorescent or chemiluminescent signal.

In one embodiment, the apparatus may include an annular septum that covers, and which may partially define, the chambers, and which permits needle access to the chambers for delivery of liquids to the chambers.

In another embodiment, one or more of the channels may contain an electrophoresis medium, such as a covalently crosslinked medium, a noncovalently crosslinked medium, or a flowable medium.

In another aspect, the invention provides a method for preparing a plurality of electrophoretic paths which are substantially bubble-free. The method may include providing an apparatus such as described above, such that the reservoir region contains a liquid or is in fluid communication with a liquid source, and centrifuging the substrate about a central axis that is perpendicular to the channels so that the liquid is dispersed from the central reservoir region into the channels and chambers, such that any air bubbles in the chambers, channels, and/or passageways are forced towards the axis of rotation, yielding a plurality of bubble-free electrophoretic paths between the reservoir and the chambers.

In an alternate embodiment, the method may include providing an apparatus such as described above such that the reservoir region, and optionally the channels, passageways, and/or chambers, contain a liquid, and centrifuging the substrate about a central axis that is perpendicular to the channels so that the liquid is dispersed from the central reservoir region into the channels and chambers, such that any air bubbles in the chambers, channels, and/or passageways are forced towards the axis of rotation, yielding a plurality of bubble-free electrophoretic paths between the reservoir and the chambers.

The apparatus and methods discussed above can also be used for sample analysis. In one aspect, the invention includes a method for analyzing a plurality of samples. The method preferably includes providing an apparatus such as describes above, such that the central reservoir region, channels, and chambers contain a liquid medium suitable for electrophoresis of such samples. Samples are provided in one or more of the sample chambers, and an electric field is applied under conditions effective to cause migration of sample(s) through at least one channel towards the central reservoir region. The channel(s) may be interrogated before, during and/or after electrophoresis to detect one or more sample components in the channel(s).

The invention may be applied to the separation and/or analysis of any of a variety of samples, particularly proteins, nucleic acids, polysaccharides, small molecules, and the like. Also, sample components to be detected may be labeled with detectable labels, e.g., fluorescent or chemiluminescent labels, to aid detection. The invention is also useful in combination with a wide variety of sample preparation methods, such as the polymerase chain reaction, oligonucleotide ligation assays, restriction fragment analysis, polymer sequencing, screening assays, and the like.

These and other features and aspects of the invention will be further understood in light of the following description and the accompanying drawings.

DETAILED DESCRIPTION OF THE PREFERRED EMBODIMENTS

The present invention is directed to devices, apparatus, and methods useful for rapidly and conveniently analyzing a plurality of samples using electrophoresis. In one aspect, the insertion provides radial channel arrays having electrophoretic pathways which, when filled with an appropriate liquid, are substantially bubble-free. The invention thus provides improved reliability in high throughput electrophoresis applications.

As used herein, the terms "channel" and "microchannel" are interchangeable.

I. Apparatus

Figure 1:
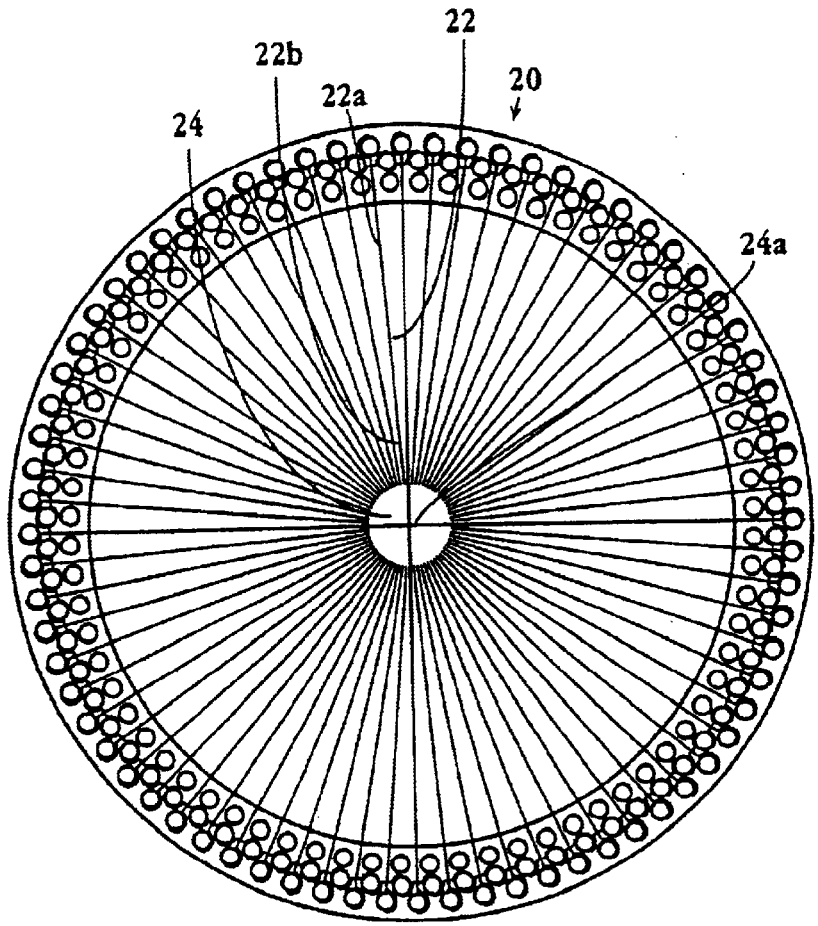
FIG. 1 shows a cross-sectional overview of a substrate in accordance with the invention.
Figure 2:
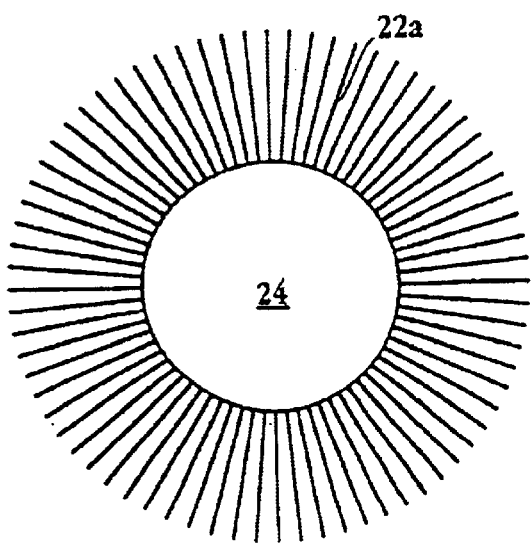
FIG. 2 shows an enlarged view of the central reservoir of the substrate from FIG. 1.

Reference is made to FIGS. 1 through 7, which illustrate various features of a radial channel array in accordance with a preferred embodiment of the invention. With reference to FIG. 1, substrate 20 defines a plurality of microchannels 22 which emanate from a central reservoir region 24. Each microchannel includes a proximal end 22a and a distal end 22b. The channels define lines that intersect at a central point or axis 24a (FIG. 2) in the center of the array. The central reservoir region 24 provides a holding area for an electrophoresis buffer which is in fluid communication with the proximal ends. The central reservoir can also be used to introduce an electrophoresis medium or wash fluid into the channels.

Figure 3:
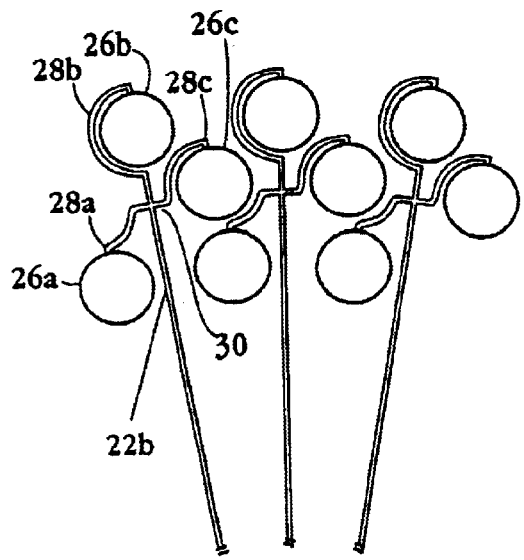
FIG. 3 shows an enlarged view of the distal end of a channel having linked by passageways to a sample chamber, a sample-receiving chamber, and a running buffer chamber.

In the embodiment shown in FIG. 3, each microchannel 22 terminates at its distal end with three chambers 26a, 26b and 26c which are linked to the distal end by connecting passageways 28a, 28b and 28c. Each chamber is linked to the associated microchannel by a passageway that connects to a radially remote region of the chamber. In other words, each passageway leads from each chamber in a direction that is initially away from the central reservoir region, to facilitate centrifugal removal of bubbles from the pathways of electrophoresis. The passageways from each of chambers 25a, 26b and 26c are preferably linked to form a T injector function 30, wherein passageways 28a and 28c each form a right angle with respect to distal microchannel end 22b at junction 30. These chambers may be used for various purposes, such as a sample chamber, running buffer chamber, and sample-receiving chamber, respectively, as discussed further below. For example, when chambers 26a and 26c are used as a sample chamber and sample-receiving chamber, an electric field between these two chambers can be used to draw a selected sample volume into junction 30, for subsequent electrophoresis towards the central reservoir region. The chambers may also be provided with in dependently controllable electrodes for controlling electrical voltages and currents in the device for various operations, such as electrodes 32a, 32b, and 32c shown in FIGS. 4A and 4B, and central electrode 32d in FIG. 4C.

Preferably, the three chambers 26a, 26b and 26c associated with each distal end 22b are located at different radial distances from the center of the substrate, to allow increased packing density of the microchannels and chambers. Thus, in FIG. 3, it can be seen that chamber 26a is closest to the substrate center, followed by chamber 26c, and then 26b, although other arrangements can also be used.

Figure 4A:
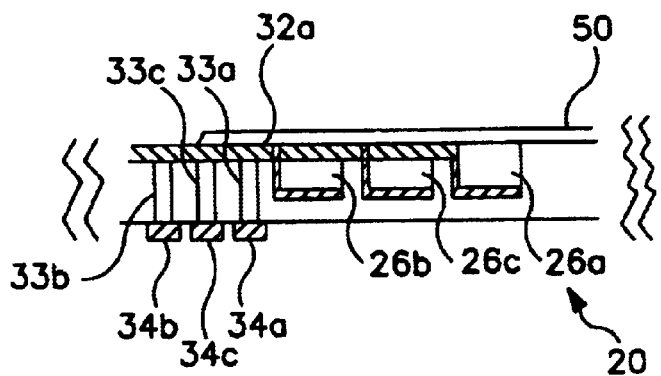
FIGS. 4A–4C show exemplary configurations for providing electrodes to the chambers and central reservoir to control electrical voltages and currents.
Figure 4B:
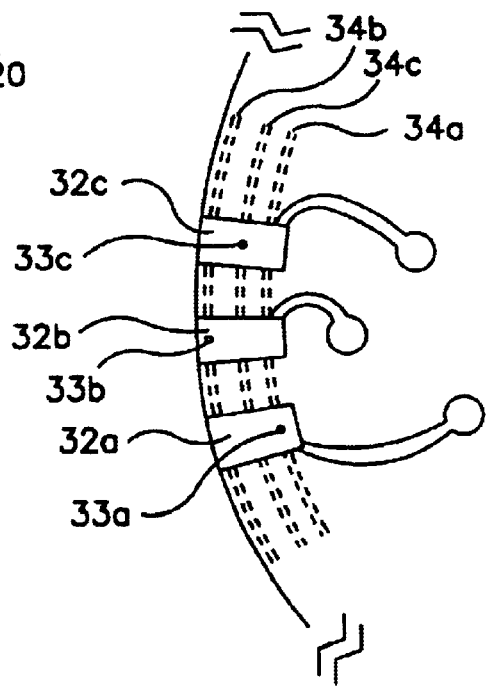

FIGS. 4A and 4B show a partial cross-sectional view, and partial overhead view, respectively, of a substrate 20 that includes chambers 26a, 206b and 26c, and electrically conductive leads (electrodes) 32a, 32b, and 32c which are disposed along the surface of the substrate and which may extend into each chamber as shown. Also shown are optional concentric ring contacts 34a, 34b, and 34c located on the other side of the substrate, which may be electrically linked to leads 32a, 32b, and 32c, respectively via connections 33a, 33b, and 33c as shown. The concentric ring contacts can be included to perform elecrophoretic separations in the channels in parallel. The chambers can be covered with an annular cover or septum 50 as discussed further with reference to FIGS. 5–7 below.

Figure 4C:
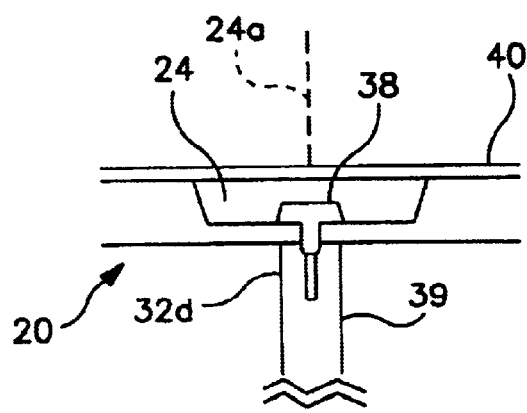

FIG. 4C shows a partial cross-sectional view of the central region of the substrate, including cover layer 40, central reservoir region 24, and a threaded fastener 38 by which the substrate can be connected to a motor shaft 39 to rotate the substrate about central axis 24a. The motor shaft is preferably electrically grounded to provide the equivalent of a fourth electrode 32d that can be used in combination with electrodes 32a, 32b, and 32c, which permit directed movement of charged species between chambers or into and through the channels. Each electrode can be connected to an independently controllable voltage source in order to control the movement of materials in the chambers and channels at appropriate times.

Although FIGS. 4A–4C show particular electrode configurations, it will be appreciated that any of a variety of other configurations can also be used. For example, the electrodes can be provided from above the chambers, e.g., as part of a cover layer bonded over the substrate in which the channels, passageways, chambers, and central reservoir are defined. Similarly, the electrode in the central reservoir can be disposed above the central reservoir, rather than through the bottom as shown at 32d in FIG. 4C.

Figure 5:
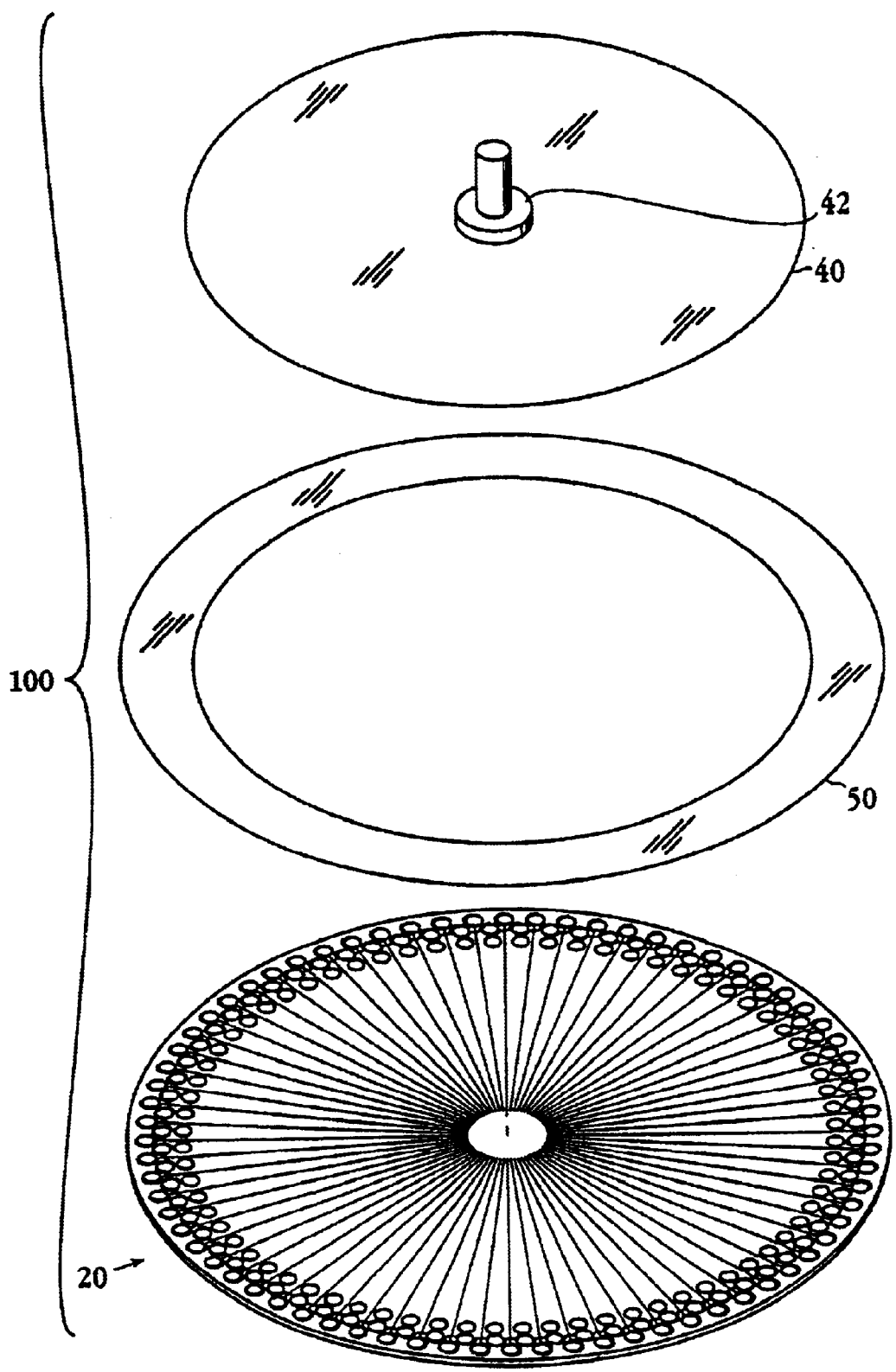
FIGS. 5, 6 and 7 illustrate an exploded perspective view, cross-sectional view, and perspective view, respectively, of a substrate assembly of the invention.
Figure 6:
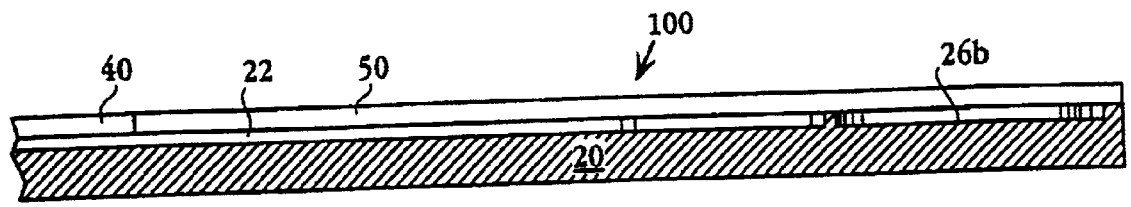
Figure 7:
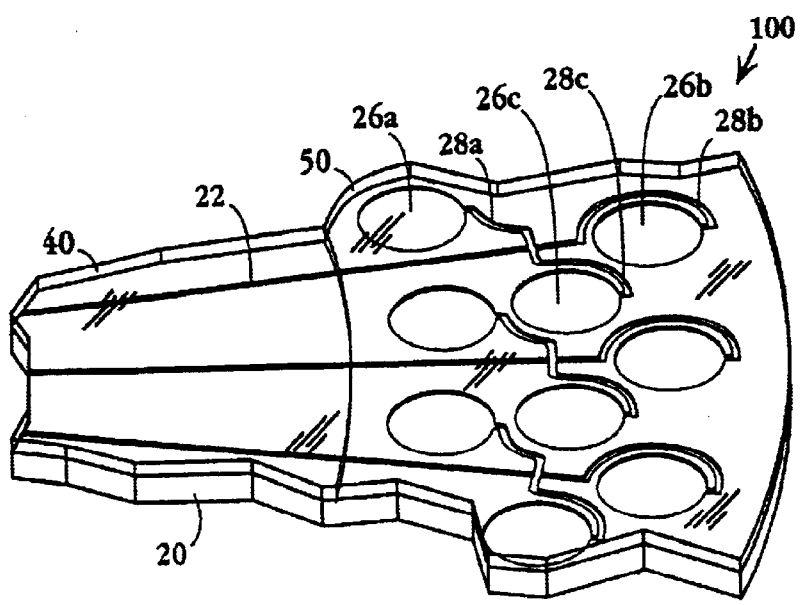

FIGS. 5–7 show an exemplary substrate assembly 100 which includes a substrate 20, a channel cover 40, and an annular chamber cover 50. Channel cover 40 can be used to cover the channel array prior to filling the array with liquid media. Cover 40 may additionally include an inlet 42 for introducing liquid into the central reservoir of the array, for dispersal into the channels. Annular chamber cover 50 is provided to cover the chambers during or after being filled with liquid.

The various features of the channel array can have any dimensions and configurations that are compatible with the utilities of the invention. Smaller dimensions are generally preferred in order to maximize the density of microchannels, to facilitate high sample throughout. For example, the microchannels can have any of a variety of cross-sectional configurations, such as square, rectangular, semicircular, circular, concave, or V-shaped, with a broad range of widths and depths. In particular, the substrate may include discrete capillary tubes as microchannels disposed upon a planar surface of the substrate. Conveniently, the channels have rectangular, square, or concave cross-sections with depths and widths usually from about 250 $\mu$m to 1 $\mu$m, more typically from 100 $\mu$m to 1 $\mu$m, and preferably 50 $\mu$m or less. Similar considerations apply to the cross-sections of the passageways which link the chambers to the distal ends of the channels.

The lengths of the channels are selected to permit a desired degree of separation of sample components, with shorter lengths providing shorter electrophoresis times at the expense of decreased separation, and longer lengths providing longer separation paths and greater separation at the expense of longer electrophoresis times. For example, channels of from 1 cm to 50 cm lengths are suitable for many separations, although longer and shorter lengths can be used as well.

The chambers at the distal ends of the microchannels can have any configuration such as circular, oval, square, and the like, and are typically circular. The sizes and configurations of the chambers linked to each microchannel can be the same or different. For example, the sample chamber should be large enough to receive a sufficient sample volume, typically 10 $\mu$L or less. More generally, it is the preferred that all of the chambers be large enough to contain a sufficient amount of buffer to avoid buffer depletion during electrophoresis.

The electrodes for generating electrical currents can be made of any suitable conductive material, and are typically made from one or more metals or alloys. Exemplary electrode materials include copper, silver, platinum, palladium, carbon, nichrome, and gold. The electrode materials can be formed by known methods, conveniently by vapor deposition, silk screen imprint, or other patterning techniques. The electrode materials may be coated with appropriate coating materials to inhibit electrochemical reactions with samples and reagents. For example, electrodes may be coated with a permeation layer having a low molecular weight cutoff that allows passage of small ions but not reagent or analyte molecules, as described, for example, in PCT Publ. No. WO 95/12808 and WO 96/01836.

The passageways leading from the chambers to the channels are preferably of minimum length to facilitate rapid electrophoresis. However, longer than minimum lengths may be useful to help avoid leakage of liquid from the chambers into the channels.

The substrate defining the channel array is preferably weighted evenly about its central axis to allow stable centrifugation. Typically, the substrate is provided in the shape of a disc having a substantially circular perimeter.

The substrate can be formed from any material, or combination of materials, suitable for the purposes of the invention. Materials which may be used will include various plastic polymers and copolymers, such as polypropylenes, polystyrenes, polyimides, and polycarbonates. Inorganic materials such as glass and silicon are also useful. Silicon is advantageous in view so its compatibility with microfabrication techniques and its high thermal conductivity, which facilitates rapid heating and cooling of the device if necessary.

The channel array may be formed by any suitable methodology available in the art. For plastic materials, injection molding will generally be suitable to form channels, etc., having a desired configuration. For silicon, standard etching techniques from the semiconductor industry may be used, as described in Madou (1997) and Sze (1988), for example. Etching techniques may be preferred for channel arrays with especially small dimensions.

The substrate typically contains two or more laminated layers. For example, the channel array can be formed by etching or injection molding into the surface of a substrate, after which the channel array is sealed by overlaying a layer of material which covers at least the channels, passageways, chambers, and optionally the central reservoir, to prevent evaporation of liquids from the array (see FIGS. 5–7).

In general, the substrate layers can be sealably bonded in a number of ways. Conventionally, a suitable bonding substance, such as a glue or epoxy-type resin, is applied to one or both opposing surfaces that will be bonded together. The bonding substance may be applied to the entirety of either surface, so that the bonding substance (after curing) will come into contact with the chambers and/or channels. In this case, the bonding substance is selected to be compatible with the sample and any detection reagents used in the assay. Alternatively, the bonding substance may be applied around the channel array so that contact with the sample will be minimal or avoided entirely. The bonding substance may also be provided as part of an adhesive-backed tape or membrane which is then brought into contact with the opposing surface. In yet another approach, the sealable bonding is accomplished using an adhesive gasket layer which is placed between the two substrate layers. In any of these approaches, bonding may be accomplished by any suitable method, including pressure-sealing, ultrasonic welding, and heat curing, for example.

The substrates and apparatus of the invention may be adapted to allow rapid heating and cooling of the chambers and channels to facilitate sample preparation e.g., or PCR) and/or sample separation. In one embodiment, the device is heated or cooled using an external temperature-controller. The temperature-controller is adapted to heat/cool one or more surfaces of the device, or may be adapted to selectively heat the detection chambers themselves. To facilitate heating or cooling with this embodiment, the substrate material is preferably formed of a material which has high thermal conductivity, such as copper, aluminum, or silicon. Alternatively, a substrate layer in contact with the chambers and/or channels may be formed from a material having moderate or low thermal conductivity, such that the temperature of the all or selected chambers and/or channels can be conveniently controlled by heating or cooling the heat-conductive layer regardless of the thermal conductivity of other layers in the substrate. In one preferred embodiment, an outer layer is provided across one of the surfaces of substrate as an adhesive copper-backed tape.

In an alternative embodiment, means for modulating the temperature of the detection chambers is provided in the substrate of the device itself. For example, the substrate may include resistive traces which contact regions adjacent the sample chambers, whereby passage of electrical current through the traces is effective to heat or cool the chambers. This approach is particularly suitable for silicon-based substrates, and can provide superior temperature control.

For optical detection, the material defining the channel array is preferably optically transparent or at least includes transparent regions or windows which permit viewing of part or all of each channel, and optionally permit viewing of the chambers, passageways, and/or other elements of the channel array. For this purpose, silica-based glasses, quartz, polycarbonate, or an optically transparent plastic layer may be used, for example. Selection of the particular transparent material will depend in part on the optical properties of the material and the spectroscopic characteristics of the signal to be detected. For example, in a fluorescence-based assay, the material should have low fluorescence emission at the wavelength(s) being measured. The window material should also exhibit minimal light absorption for the signal wavelengths of interest.

Other layers or materials may also be included. For example, the sample chamber may be lined with a material that has high heat conductivity, such as silicon or a heat-conducting metal, to permit rapid heating and cooling of the sample. Silicon surfaces which contact the sample are preferably coated with an oxidation layer or other suitable coating, to render the surface more inert. Similarly, where a heat-conducting metal is used in the substrate, the metal can be coated with an inert material, such as a plastic polymer, to prevent corrosion of the metal and to separate the metal surface from contact with the sample.

For electrophoresis of samples, the channel array is preferably filled with an electrophoresis medium via the central reservoir region. For this purpose, the central reservoir region and channels may be enclosed using a cover equipped with an inlet, for transporting liquid into the array, and the distal chambers can be covered with an annular cover, such as cover 50 in FIG. 5.

In one embodiment, the annular cover is porous to air but is relatively impervious to aqueous liquid. Thus, with reference to FIG. 5, liquid introduced through inlet 42, e.g., by pressure or by centrifugal force, flows through the radial channels and into the distal chambers such that displaced air escapes through the annular cover. Once the chambers are full, the porous cover provides back pressure sufficient to prevent the liquid from leaking out of the chambers. The porous annular cover may then be replaced with an annular septum to seal the chambers but allow introduction of fluids to the channels by cannula or needle. In an alternate approach, an annular cover, which may be porous or not, is placed in close (but not sealed) contact with the outer radial region of the substrate during filling, so that excess liquid escapes through a narrow gap between the annular surface and outer substrate surface. After filling is complete, the annular ring can be pressed securely against the opposing substrate surface to seal the chambers, such that excess liquid between the annular ring and substrate surfaces is squeezed out. Filling can be promoted further by placing the substrate assembly in a vacuum atmosphere, to help reduce resistance from any air occupying the channels and chambers.

Figure 8:
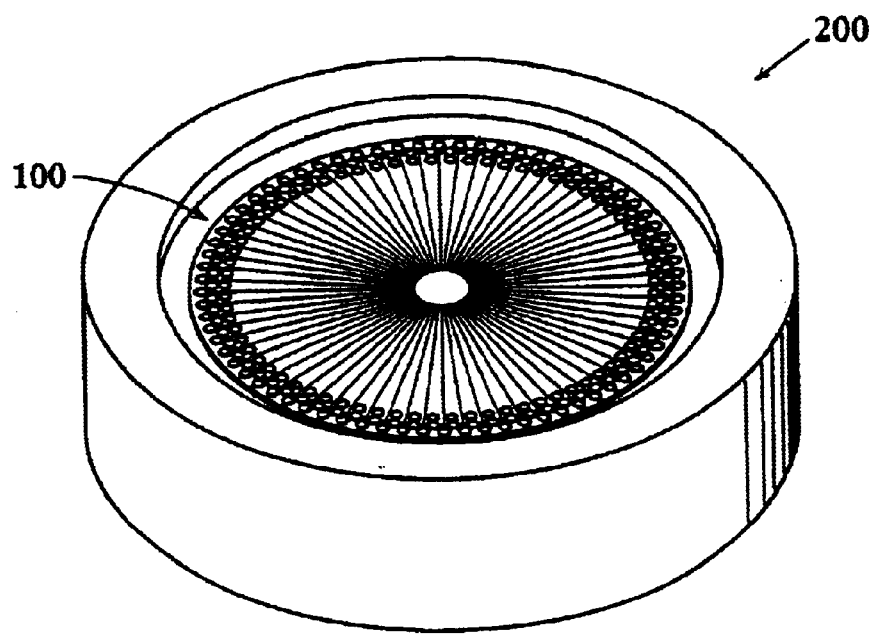
FIG. 8 illustrates a centrifugal device for introducing liquid into a channel array of the invention with liquids and for removing air bubbles.

According to one aspect of the invention, filling the channel with liquid can be facilitated by spinning the array about the central axis perpendicular to the array plane, to drive fluid towards the periphery of the array by centrifugal force. In addition, any bubbles in the chambers will be driven towards the center of the array, away from the passageways linking the chambers to the channels. In this regard, FIG. 8 shows a substrate assembly 100 seated in a centrifugation device 200, for centrifuging the assembly as just described. The substrate assembly 100 is spun at a speed and for a time sufficient to remove substantially all bubbles from the channels and passageways, to provide continuous electrical and liquid pathways between the central reservoir and the chamber electrodes.

The electrophoresis medium in the channels can be any medium deemed appropriate by the user for the purposes of this invention. Usually, the medium will be an aqueous medium, although nonaqueous media are also contemplated. Additionally, the medium may contain agents that impede or otherwise alter the migration rates of sample components. Examples of such agents include water-soluble polymers such as agarose, polyacrylamide, polymethacrylamide, methyl cellulose, hydroxyethylcellulose, hydroxypropylcellulose, hydroxypropylmethylcellulose, polyethylene glycol, galactomannan, polyvinyl alcohol, polyacryloylaminoethoxyethanol, polyethylene imine, polyvinylacetate, polyvinylpyrrolidone, and polyvinyloxazolidone, and also fluorine-containing polymers (e.g., see Ramakrishna et al., U.S. Pat. Nos. 5,552,028 and 5,567,292; Grossman, U.S. Pat. No. 5,374,527; Menchen et al., U.S. Pat. No. 5,468,365; and Grossman et al. (1992)). The foregoing materials can be used to form entangled matrices if concentrations are sufficiently high, although more dilute (non-entangled) concentrations may also be used. Covalently crosslinked media, such as polyacrylamide crosslinked with bis-acrylamide, can also be used, in which case loading is typically accomplished before the medium is crosslinked, e.g., by UV irradiation or by adding an initiator reagent such as tetramethylenediamine plus ammonium persulfate.

If desired, the inner surfaces of all or part of the chananel array can be coated with any suitable coating material, to reduce sample adsorption. Since electrophoresis is usually performed in an aqueous separation medium, adsorption of sample can usually be reduced by covering the inner surfaces of the separation cavity with a hydrophilic coating that masks potentially adsorptive surface regions. Exemplary reagents for coating adsorptive surfaces include poyacrylamide, polymethacrylamide, polyvinyl alcohol, polyethers, cellulose acetate, polyalkylene oxides, poly (vinyl pyrrolidone), and other materials as are known in the art. Preferably, such coatings are attached to interior surfaces covalently, although adsorptive noncovalent coatings may also be suitable.

Coating reagents for reducing sample adsorption can also be used to control the magnitude of electroosmotic flow (EOF). For example, EOF along glass silicate surfaces can be substantially reduced by coating them with a neutral reagent that masks a substantial percentage of surface silanol groups. The magnitude of EOF can be further controlled by using coating reagents that include positively or negatively charged groups. Positively charged coatings can be used to nullify surface negative charges to give a net surface charge of zero, so that EOF=0. Coatings with higher positive charge densities can be used to reverse the direction of EOF for charged surface materials. This can be useful for slowing the net migration rates of positively charged sample species. Conversely, negatively charged coatings can be used to impart to or increase the magnitude of negative charge on surfaces, to slow the net migration rates of negatively charged species. Representative positively charged coatings include polyethyleneimine, quaternized polyethyleneimine, and chitosans, for example. Representative negatively charged coatings include carboxylate and sulfonate containing materials, such as poly(methylglutamate) and 2-acrylamido-2-methylpropanesulfonate polymers, for example. It will be recognized that charged coatings can also effectively reduce sample adsorption, especially for samples having the same charge polarity as the coating (e.g., Wiktorowicz, U.S. Pat. Nos. 5,015,350 and 5,181,999).

The choice additives, if preset in the separation medium will depend in part on the sample and the nature of the interior surfaces, as well as other factors. In some applications, it may be desirable to use both a covalent surface coating and soluble buffer agents to control sample adsorption and EOF.

Samples may be from any source which can be dissolved or extracted into a liquid that is compatible with the uses of present invention, and which may potentially contain one or more analytes of interest. For example, the sample may be a biological fluid such as blood, serum, plasma, urine, sweat, tear fluid, semen, saliva, cerebral spinal fluid, or a purified or modified derivative thereof. Amples may also be obtained from plants, animal tissues, cellular lysates, cell cultures, microbial samples, and soil samples, for example. The sample may be purified or pre-treated if necessary before testing, to remove substances that might otherwise interfere with analyte detection. Typically, the sample fluid will be an aqueous solution, particularly for polar analytes such as polypeptides, polynucleotides, and salts, for example. The solution may include surfactants or detergents to improve analyte solubility. For non-polar and hydrophobic analytes, organic solvents may be more suitable.

For each channel, sample is preferably loaded into a distal chamber, referred to herein as a sample chamber, by injection through a chamber wall, e.g., via a septum material such as discussed above. Pre-existing air and/or liquid in the chamber is preferably allowed to escape the chamber via a second needle of cannula which passes through the chamber wall, so that the chamber is preferably uniformly loaded with the sample. One or more of the other distal chambers of each channel can also be loaded with a selected liquid medium using the same loading technique. Sample loading can be automated using a robotically controlled sample dispensor, if desired.

After sample, loading is complete, the substrate may be centrifuged as discussed above with respect to FIG. 7, in order to drive any air bubbles towards the center of the channel array, and out of the various paths of electrophoresis.

Once loaded, an aliquot of sample is preferably transferred from the sample chamber to the distal end of the channel by applying an electric field between the sample-containing chamber and a selected "sink" (waste) chamber. For example, with reference to FIG. 3, sample in chamber 25a can be transferred electrokinetically into junction 30 by applying an electric field between chambers 26a and 26c. The amount of sample (sample plug) transferred into the pathway of channel 22 is proportional to the cross-sections of passageways 28a and 28c at junction 30 (which defines the initial band width of the aliquot) and by the cross-section of channel 22 at junction 30. After the first electric field is shut off, an electric field is applied between chamber 26b and central reservoir 24, thereby drawing the sample plug into channel 22 and initiating separation of sample components on the basis of different electrophoretic mobilities. Any other appropriate sample loading sequence may also be used.

Electrophoretic operations can be carried out in the channels simultaneously (in parallel), individually (sequentially), or any combination thereof. With reference to FIGS. 4A–4C discussed above, electrophoresis can be performed sequentially by applying appropriate voltages to electrodes 32a, 32b, 32c, and 32d (without needing rings 34a–34c and connectors 33a –33c). Conveniently, this can be accomplished by attaching an electrical contact card to the upper or lower surface of the substrate, such that the contact card has individual electrical contacts that align with the substrate electrodes, as illustrated in FIGS. 10A–10C.

Figure 10A:
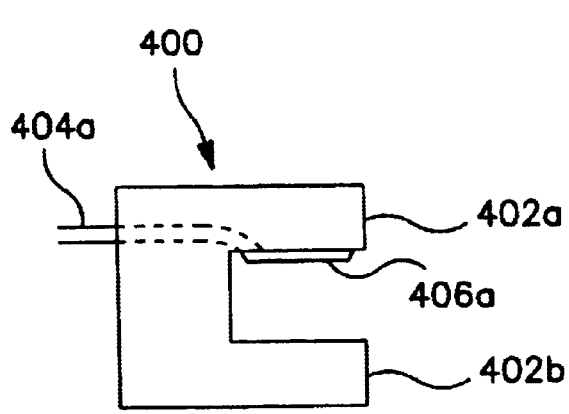
FIGS. 10A–10C illustrate an embodiment in which electrical voltages are provided to the substrate by a contact card.
Figure 10B:
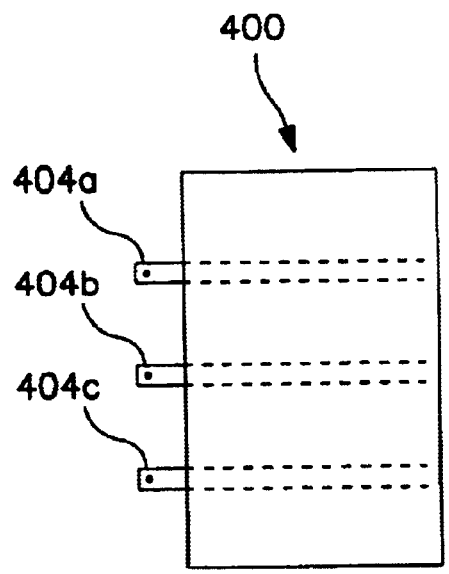
Figure 10C:
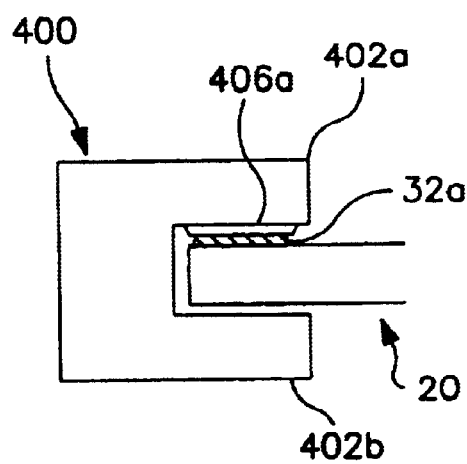

FIGS. 10A–10C show a cross-sectional side view and overhead view of an exemplary contact card 400 which can be used to supply separate electrical voltages to the distal chambers of a microchannel. Contact card 400 includes upper and lower protrusions 402a and 402b which define a cavity therebetween, for snugly gripping an electrical lead on the substrate, such as electrical leads 32a, 32b and 32c (FIGS. 4B and 10C). The upper and lower protrusions of the card are preferably made of a flexible material so that the contact card can be easily clamped onto and removed from substrate 20. Contact card 400 also includes electrical leads 404a, 404b, and 404c having exposed terminal ends 406a, 406b, and 406c, respectively, for contacting electrical leads 32a, 32b, and 32c, as illustrated in cross-sectional side view in FIG. 10C.

Figure 11B:
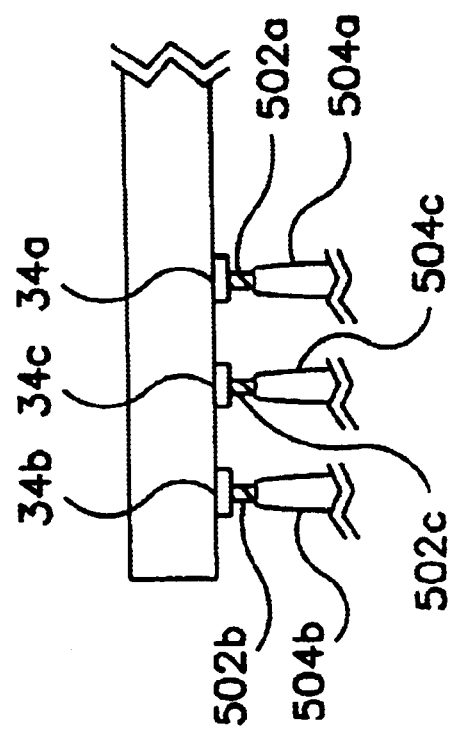
FIGS. 11A–11B illustrate an embodiment in which electrical voltages are provided to the substrate by brush contacts.
Figure 11A:
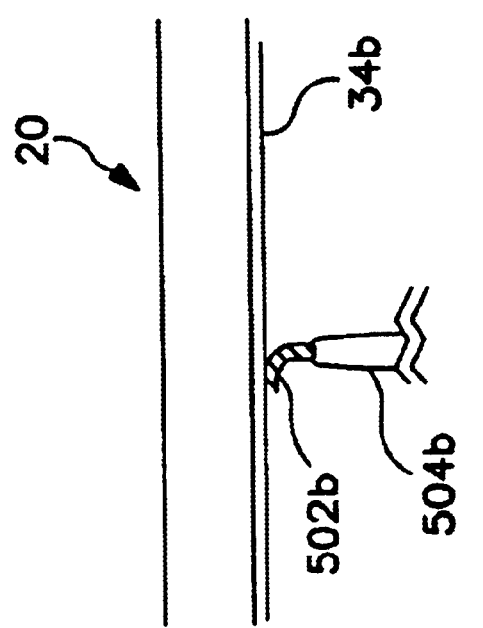

Simultaneous electrophoretic operations can be performed conveniently by applying appropriate voltages to one or more conductive rings which are electrically connected to the electrodes in the distal chambers, such as rings 34a, 34b and 34c shown in FIGS. 4A and 4B. For this embodiment, the voltage potentials are preferably provided through conductive brushes which can remain in contact with the concentric rings while the substrate is rotated about its axis for analyte detection, if desired. For example, with reference to FIGS. 11A and 11B, a substrate 20 having concentric ring contacts such as contacts 34a, 34b, and 34c shown in FIG. 4A, is contacted with corresponding brush contacts 502a, 502b, and 502c which are held by one or more holders, such as holders 504a, 504b, and 504c.

Simultaneous electrophoresis has the advantage of faster sample analysis. Sequential electrophoresis, on the other hand, allows more careful control of electrophoresis conditions in each channel.

Sample components of interest may be detected in the channels by any of a variety of techniques, such as fluorescence detection, chemiluminescence detection, UV-visible adsorption, radioisotope detection, electrochemical detection, and biosensors, for example. For optically based detection methods (e.g., fluorescence, absorbance, or chemiluminescence), the substrate assembly should contain at least one detection zone near the proximal end of each channel.

Typically, optical detection is performed from above or below the plane of the substrate assembly. In general, optical signals to be detected will involve absorbance or emission of light having a wavelength between about 180 nm (ultraviolet) and about 50 $\mu$m (far infrared) More typically, the wavelength is between about 200 nm (ultraviolet) and about 800 nm (near infrared). For fluorescence detection, any opaque substrate material in the zone of detection preferably exhibits low reflectance properties so that reflection of the illuminating light back towards the detector is minimized. Conversely, a high reflectance will be desirable for detection based on light absorption. With chemiluminescence detection, where light of a distinctive wavelength is typically generated without illuminating the sample with an outside light source, the absorotive and reflective properties of the substrate assembly will be less important, provided that at least one optically transparent window is present per channel for detecting the signal. Preferably, substantially all of the substrate assembly is transparent, to allow visualization of the entire channel array.

When the material defining the upper surface and sides of the channels are optically clear, and detection involves fluorescence measurement, the channels can be illuminated with excitation light through the sides of the channels (parallel to the plane of the substrate assembly), or more typically, diagonally from above (e.g., at a 45 degree angle), and emitted light is collected from above the substrate assembly, usually in a direction perpendicular to the plane of the channel array.

Figure 9:
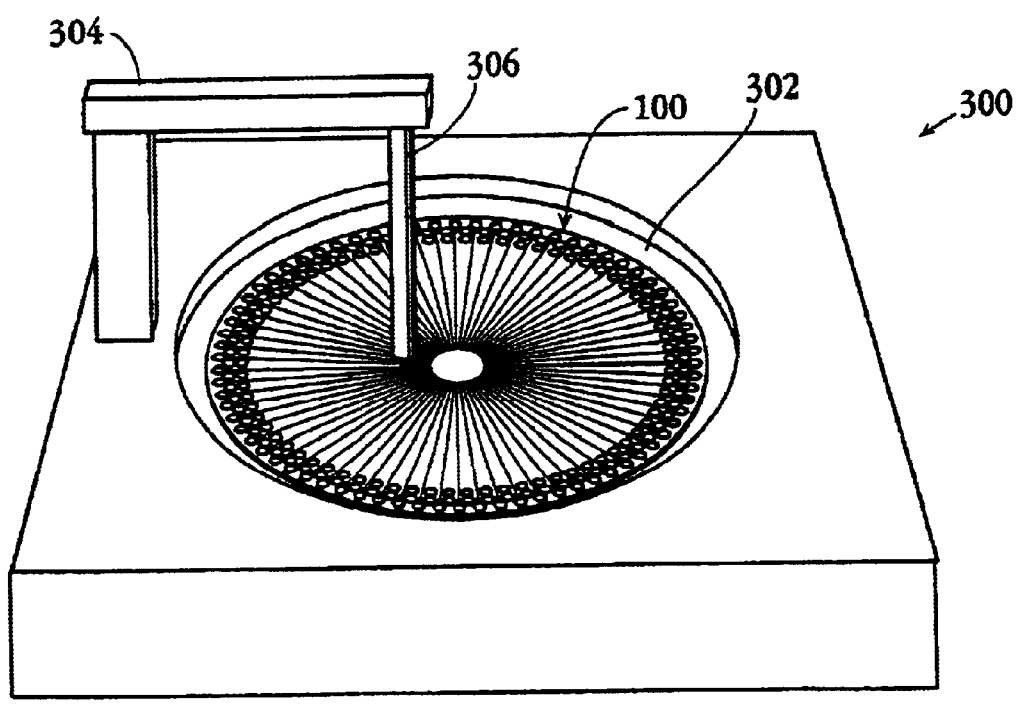
FIG. 9 shows a rotary detector for detecting and/or monitoring sample components in the channels.

FIG. 9 shows an exemplary detection system 300 comprising a rosary plate 302, substrate assembly 100, and detector arm 304. Detector arm 304 carries a detector rod 305 having a lower end that is positioned over a selected detection zone on the channel array of assembly 100. In operation, detector rod 306 is positioned over a detection zone of a channel for a time (or times) sufficient to collect a signal from the channel to identify the presence of, and/or quantify, one or more sample components in the channel.

In one approach, the detector rod remains over the detection zone of the channel during electrophoretic separation of the sample, to record an electropherogram of components continuously or at discrete time points as they migrate past the detector rod. After the desired information has been collected, assembly 100 is rotated so that the detector is positioned over the detection zone in the next channel, and another electropherogram is recorded. Thus, electrophoresis is performed sequentially from channel to channel, until the desired electropherograms have been obtained.

In another approach, signals are measured periodically in each channel during simultaneous electrophoresis in two or more channels, by rotating the assembly at selected time intervals to collect electropherograms simultaneously as a series of time points. Preferably, the frequency of data collection from each channel is sufficient to ensure collection of at least two points, and preferably more, per component peak, to facilitate accuracy and sensitivity of detection.

The sample components or analytes to be measured can be labeled to facilitate sensitive and accurate detection. Labels may be direct labels which themselves are detectable or indirect labels which are detectable in combination with other agents. Exemplary direct labels include but are not limited to fluorophores, chromophores, (e.g. $^{32}$P, $^{35}$S, $^{3}$H) spin-labels, chemiluminescent labels (e.g., dioxetane-producing moieties), radioisotopes, and the like. Exemplary indirect labels include enzymes which catalyze a signal-producing event, and ligands such as an antigen or biotin which can bind specifically with high affinity to a detectable anti-ligand, such as a labeled antibody or avidin. Many references on labeling molecules of interest, such as DNA, proteins, polysaccharides, and the like, are available. Exemplary references include Matthews et al. (1988), Haugland (1992), Keller and Manak (1993), Eckstein (1991), Fung et al.; Hobbs et al., Lee et al., Menchen et al., Bergot et al., Rosenblum et al. (1997), and Jackson (WO 91/05256).

In one preferred embodiment, sample components or target analytes are measured by fluorescence detection. To perform such detection, the detection zone of each channel can be illuminated by a suitable light source, e.g. a high intensity mercury vapor lamp, laser, or the like. Preferably the illumination means is a laser having an illumination beam at a wavelength between 488 and 550 nm. More preferably, particularly for dye-labeled polynucleotides, illumination is accomplished using a laser light generated by an argon ion laser, particularly the 488 and 514 nm emission lines of an argon ion laser, or the 532 nm emission line of a neodymium solid-state YAG laser. Several argon ion lasers are available commercially which lase simultaneously at these lines, e.g. Cyonics, Ltd. (Sunnyvale, Calif.) Model 2001, or the like. The fluorescence is then detected by a light-sensitive detector, e.g. , a photomultipier tube, a charged coupled device, or the like. Conveniently, the fluorescence detector has a confocal arrangement, such as described in Huang et al., 1992, Kheterpal et al., (1995) and other references (see also Fodor, 1995, and Mathies et al., 1992).

Sample component signals can also be collected from one or more channels simultaneously using an area-type detector, such as a charge-coupled detector (CCD), (e.g., Model TE/CCD512SF, Princeton Instruments, Trenton, N.J.) with suitable optics (Ploem, 1993), such as described in Yershov et al. (1996), or may be imaged by TV monitoring (Khrapko, 1991). For radioactive signals (e.g., $^{32}$P), a phosphorimager device can be used (Johnston et al., 1990; Drmanac et al , 1992; 1993). Other commercial suppliers of imaging instruments include General Scanning Inc. (Watertown, Mass., www.genscan.com), Genix Technologies (Waterloo, Ontario, Canada; www.confocal.com), and Applied Precision Inc.

III. Utility

The present invention can be used for any of a wide variety of applications. The invention can be used for medical or veterinary purposes, such as detecting pathogens, diagnosing or monitoring disease, genetic screening, determining antibody or antigen titers, detecting and monitoring changes in health, and monitoring drug therapy. The invention is also useful in a wide variety of forensic, environmental, and industrial applications, including screening molecules for selected activities.

For example, the invention can be used to analyze varoius nucleotide and polynucleotide analytes produced by a variety of techniques, such as the polymerase chain reaction, oligonucleotide ligation assay (e.g., Whiteley, et al. and Landegren et al.), minisequencing (Pastinen, et al., 1997), microsatellite/variable number or tandem repeat (VNTR) analyses (e.g., Livak et al.), restriction fragment length polymorphism. (RFLP) analysis, and Sanger-type sequencing (e.g., Lee et al., EP 805190 A2, pp. 38–39)

The invention is also useful for analyzing other types of sample components, such as polypeptides, amino acids, polysaccharides, monosaccharides, metabolites, drugs, etc. The invention is also useful for high-throughput screening, wherein a large number of different molecules are tested for a selected activity, such as binding of a ligand to a receptor, activation or inhibition of an enzyme, and the like.

More generally, the present invention provides a convenient way to rapidly analyze analytes in a plurality of samples. The invention is highly flexible in its applications, being adaptable to analysis of a wide variety of analytes and sample materials. Furthermore, for array configurations in which distal chambers are linked to the channels by passageways leading away from the center of the array, the invention allows bubbles to be removed from electrophoretic paths by centrifugation, prior to sample separation and analysis, thereby enhancing precision, accuracy and reproducibility of analyses. Moreover, very small volumes of sample are required since the dimensions of channel arrays of the invention can be very small.

While the invention has been described with reference to certain embodiments and examples, it will be appreciated that various modifications and variations can be made without departing from the spirit of the invention.

What is claimed is:

1. Apparatus for electrophoretic separation of analytes, the device comprising:
    a substrate including
        (1) a central reservoir region,
        (2) a plurality or electrophoretic channels in fluid communication with, and emanating substantially radially from, the central reservoir region, the channels being coplanar with each other, and each channel having (i) a proximal end which is linked to the central reservoir region, and (ii) a distal end, and
        (3) for each channel one or more chambers that are each linked by a passageway in fluid communication with the distal end of that channel,
    wherein each passageway leads from each chamber in a direction that is initially away from the central reservoir region, whereby centrifugation of the substrate about a central axis that is perpendicular to the plane of the channels is effective to disperse liquid from the central reservoir region into said channels and chambers such that any air bubbles in the chambers, channels, and passageways are forced towards the axis of rotation, when such liquid is present in the central reservoir region.

2. The apparatus of claim 1, wherein the distal end of each channel is linked by passageways to two chambers.

3. The apparatus of claim 1, wherein the distal end of each channel is linked by passageways to a sample chamber, a sample-receiving chamber, and a running buffer chamber.

4. The apparatus of claim 1, which further includes electrodes or applying a voltage potential between said chambers and the central reservoir region.

5. The apparatus of claim 1, which further includes a detector for detecting selected components which may be present in one or more of the channels.

6. The apparatus of claim 5, wherein the detector is a fluorescence or chemiluminescence detector.

7. The apparatus of claim 5, wherein the detector is rotatable about the central axis within the central reservoir region, for detecting signal emission from each of the channels at a selected distance from the axis.

8. The apparatus of claim 5, which further includes a mechanism for rotating the substrate about the central axis such that the channels pass sequentially by the detector, for detecting one or more components that may be present in the channels.

9. The apparatus of claim 1, wherein said chambers are defined in part by an annular septum that covers the chambers and permits needle-access to the chambers for delivery of liquid to the chambers.

10. The apparatus of claim 1, wherein at least one of said channels contains an electrophoresis medium.

11. The apparatus of claim 10, wherein the electrophoresis medium is a flowable medium.

12. The apparatus of claim 10, wherein the electrophoresis medium is a covalently crosslinked medium.

13. The apparatus of claim 1, wherein the substrate defines at least 20 of said channels.

14. The apparatus of claim 1, wherein said channels have cross-sectional diameters between 1 and 100 $\mu$m.

15. The apparatus of claim 12, wherein said channels have cross-sectional diameters between 2 and 50 $\mu$m.

16. A method for preparing a plurality of electrophoretic paths which are substantially bubble-free, comprising
    providing an apparatus as defined in claim 1 such that the reservoir region either contains a liquid or is in fluid communication with a liquid source,
    centrifuging the substrate about a central axis that is perpendicular to the channels so that the liquid is dispersed from the central reservoir region into said channels and chambers, such that any air bubbles in the chambers, channels, and/or passageways are forced towards the axis of rotation, yielding a plurality of bubble-free electrophoretic paths between said reservoir and said chambers.

17. A method for preparing a plurality of electrophoretic paths which are substantially bubble-free, comprising
    providing an apparatus as defined in claim 1 such that the reservoir region, and optionally the channels, passageways, and/or chambers contain a liquid,
    centrifuging the substrate about a central axis that is perpendicular to the channels so that the liquid is dispersed from the central reservoir region into said channels and chambers, such that any air bubbles in the chambers, channels, and/or passageways are forced towards the axis of rotation, yielding a plurality of bubble-free electrophoretic paths between said reservoir and said chambers.

18. A method for analyzing a plurality of samples comprising:
    providing an apparatus in accordance with claim 1, such that the central reservoir region, channels, and chambers contain a liquid medium suitable for electrophoresis of such samples,
    applying an electric field under conditions effective to cause migration of sample through at least one of said channels towards the central reservoir region, and
    interrogating at least one of the channel(s) to detect one or more sample components in the channel(s).

19. The method of claim 18, wherein the components to be detected are nucleic acids.

20. The method of claim 19, wherein the nucleic acids to be detected are fluorescently labeled.

21. The method of claim 19, wherein the samples are prepared by polymerase chain reaction amplification of one or more selected target sequences.

22. The method of claim 19, wherein the samples are prepared by ligating at least two oligonucleotides when the oligonucleotides are bound to adjacent regions or a target polynucleotide that are complementary to the at least two oligonucleotides.

23. The method of claim 18, wherein the components to be detected are polypeptides.

* * * * *

UNITED STATES PATENT AND TRADEMARK OFFICE
CERTIFICATE OF CORRECTION

PATENT NO.    : 6,660,147 B1
DATED         : December 9, 2003
INVENTOR(S)   : Woudenberg et al.

It is certified that error appears in the above-identified patent and that said Letters Patent is hereby corrected as shown below:

Title page,
Item [45], Date of Patent, change "*Dec. 9, 2003" to -- Dec. 9, 2003 --,
Item [*] Notice, delete "This patent is subject to a terminal disclaimer."

Signed and Sealed this

Thirteenth Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,660,147 B1
DATED : December 9, 2003
INVENTOR(S) : Woudenberg et al.

It is certified that error appears in the above-identified patent and that said Letters Patent is hereby corrected as shown below:

Drawings,
Sheet 1, Fig. 1, change the reference numeral "22a" to -- 22b --.
Sheet 1, Fig. 1, change the reference numeral "22b" to -- 22a --.
Sheet 1, Fig. 2, change the reference numeral "22a" to -- 22 --.

Column 13,
Line 29, change "plurality or" to -- plurality of --.
Line 53, change "electrodes or" to -- electrodes for --.

Column 14,
Line 62, change "regions or" to -- regions of --.

Signed and Sealed this

Seventh Day of February, 2006

JON W. DUDAS
*Director of the United States Patent and Trademark Office*